(12) United States Patent
Kuriyama

(10) Patent No.: US 11,173,148 B2
(45) Date of Patent: Nov. 16, 2021

(54) ZERO-ORDER RELEASE PREPARATION COMPOSITION FOR ANIMALS

(71) Applicant: DS PHARMA ANIMAL HEALTH CO., LTD., Osaka (JP)

(72) Inventor: Teruaki Kuriyama, Higashiosaka (JP)

(73) Assignee: DS PHARMA ANIMAL HEALTH CO., LTD., Osaka (JP)

(*) Notice: Subject to any disclaimer, the term of this patent is extended or adjusted under 35 U.S.C. 154(b) by 0 days.

(21) Appl. No.: 16/867,773

(22) Filed: May 6, 2020

(65) Prior Publication Data

US 2020/0323826 A1 Oct. 15, 2020

Related U.S. Application Data

(62) Division of application No. 16/307,544, filed as application No. PCT/JP2017/021258 on Jun. 8, 2017, now abandoned.

(30) Foreign Application Priority Data

Jun. 9, 2016 (JP) .................................. 2016-115580

(51) Int. Cl.

| A61K 31/423 | (2006.01) |
|---|---|
| A61K 47/14 | (2017.01) |
| A61K 47/26 | (2006.01) |
| A61K 47/44 | (2017.01) |
| A61P 25/08 | (2006.01) |
| A61K 47/12 | (2006.01) |
| A61K 47/36 | (2006.01) |
| A61K 9/00 | (2006.01) |
| A61K 9/20 | (2006.01) |
| A61K 47/38 | (2006.01) |

(52) U.S. Cl.
CPC .......... *A61K 31/423* (2013.01); *A61K 9/0002* (2013.01); *A61K 9/2018* (2013.01); *A61K 9/2054* (2013.01); *A61K 47/12* (2013.01); *A61K 47/14* (2013.01); *A61K 47/26* (2013.01); *A61K 47/36* (2013.01); *A61K 47/44* (2013.01); *A61P 25/08* (2018.01); *A61K 47/38* (2013.01)

(58) Field of Classification Search
CPC ............................... A61K 31/423; A61P 25/08
See application file for complete search history.

(56) References Cited

U.S. PATENT DOCUMENTS

| 6,489,350 B1 | 12/2002 | Benedyk |
|---|---|---|
| 6,750,249 B1 | 6/2004 | Yamaguchi et al. |
| 2004/0142992 A1 | 7/2004 | Scellenberger |
| 2007/0148237 A1* | 6/2007 | McKinney .......... A61K 9/5084 424/468 |
| 2011/0046072 A1 | 2/2011 | Kanikanti et al. |
| 2011/0189244 A1 | 8/2011 | Derrieu et al. |
| 2012/0322782 A1 | 12/2012 | Narishetty et al. |
| 2017/0360715 A1* | 12/2017 | Alderborn ............ A61K 9/2081 |
| 2018/0311167 A1* | 11/2018 | Li ........................ A61K 9/0065 |

FOREIGN PATENT DOCUMENTS

| CN | 102949365 | 3/2013 |
|---|---|---|
| EP | 0 168 044 | 1/1986 |
| JP | 54-163823 | 12/1979 |
| JP | 62-10012 | 1/1987 |
| JP | 2000-119181 | 4/2000 |
| JP | 2003-509349 | 3/2003 |
| JP | 2006-507251 | 3/2006 |
| JP | 2009-517394 | 4/2009 |
| JP | 2011-519878 | 7/2011 |
| JP | 2011-173881 | 9/2011 |
| JP | 2011-528702 | 11/2011 |
| JP | 2013-147513 | 8/2013 |

OTHER PUBLICATIONS

Dewey, J Am Anim Hosp Assoc, 40, 4, 2004 (Year: 2004).*
International Search Report dated Jul. 4, 2017 in International Application No. PCT/JP2017/021258.
International Preliminary Report on Patentability dated Dec. 13, 2018 in International Application No. PCT/JP2017/012158.
DS Pharma Animal Health, Consave (registered trademark) Jo (Seihin Galvo) [online], Oct. 2014, [retrieval date Jun. 23, 2017 (Jun. 23, 2017) ], Internet: <URL: http://www .ds-vet . jp/medic/ product info/pamph/ko 001b.pdf>, entire text, particularly, p. 21, with partial English translation.
Podell M. et al., 2015 ACVIM Small Animal Consensus Statement on Seizure Management in Dogs, Journal of Veterinary Internal Medicine, 2016. 02. 22, vol. 30, Issue 2, p. 477-490, [online], [retrieved on Jun. 26, 2017], Retrieved from the Internet.
Extended European Search Report dated Feb. 13, 2020 in corresponding European Patent Application No. 17810381.8.

* cited by examiner

*Primary Examiner* — Susan T Tran
*Assistant Examiner* — William Craigo
(74) *Attorney, Agent, or Firm* — Wenderoth, Lind & Ponack, L.L.P.

(57) ABSTRACT

The present invention relates to a sustained-release pharmaceutical composition intended for animal use, which comprises a drug, a sugar, a wax, and a water-soluble polymer.

5 Claims, 7 Drawing Sheets

ZERO-ORDER RELEASE PREPARATION COMPOSITION FOR ANIMALS

TECHNICAL FIELD

The present invention provides a sustained-release composition intended for animal use. For example, the present invention relates to a novel sustained-release formulation of zonisamide.

BACKGROUND ART

It is burdensome for an animal guardian to medicate a pet animal suffering from a chronic disease. In particular, when required to administer medicine a few times a day, the animal guardian could be forced to have a heavy burden in everyday life, and also could hardly achieve compliance with the medication.

In order to reduce the administration frequency of an oral drug for human from plural times a day to once a day, in general, the sustained-release technique in a formulation is first chosen. That is, such technique makes once-daily treatment possible by getting an active ingredient released gradually from a formulation in the gastrointestinal tract after administration, and getting the released active ingredient absorbed into the gastrointestinal tract over a long time. However, such sustained-release mechanism requires a formulation to move in the gastrointestinal tract over a long time. Thus, it has been thought difficult to apply the technique to carnivorans such as dogs and cats which have relatively short gastrointestinal tract.

For example, in dog's gastrointestinal tract, it depends on types of dog, but generally, a administered solid drug passes the upper gastrointestinal tract which takes the central role in the absorptive function in a limited short time. Thus, even if a general sustained-release formulation is administered, the formulation is excreted before all the active ingredient is released, i.e., it is hard to obtain an useful bioavailability. In the contrary, even if a sustained-release formulation having a fast release rate is tried to obtain an useful bioavailability, it is hard to control the release rate for such short time, that is, the release will eventually become burst-like, which is not different from a normal formulation. In this way, it has been difficult to realize a sustained-release formulation for dogs or the like.

In particular, epilepsy is one of chronic diseases whose symptom needs to be suppressed in pet animals such as dogs. Epilepsy does not put someone into abnormal behavior in normal times, but once the attack of epilepsy starts, severe symptoms such as convulsion and faint could develop. Thus, it is necessary for its patients to take an antiepileptic drug every day in order to prevent the attack. As an antiepileptic drug intended for dogs, zonisamide has been already offered commercially, but zonisamide needs to be taken twice a day. Thus, it has been desired to develop a new drug formulation which makes possible once-a-day medication to reduce guardian's burden.

PRIOR ART

Patent Reference

[Patent Literature 1] JP S54-163823 A
[Patent Literature 2] JP 2003-509349 A
[Patent Literature 3] JP 2006-507251 A
[Patent Literature 4] JP 2013-147513 A

Non-Patent Reference

[Non-Patent Literature 1] Package insert of CON-SAVE™, DS Pharma Animal Health Co., Ltd.

SUMMARY OF INVENTION

Technical Problem

The purpose of the present invention is to provide a sustained-release formulation intended for pet animals such as dogs and cats which have relatively short gastrointestinal tract. For example, it is to provide a formulation comprising zonisamide which makes possible once-a-day medication to reduce guardian's burden, said zonisamide is an antiepileptic drug requiring twice-a-day medication.

Solution to Problem

The present inventors have extensively studied to reach the above purpose, i.e., to find an ideal formulation to complete the drug dissolution within a short time in a lenear release pattern (zero-order release) which is not burst-like release, and then have found that a drug composition comprising a drug, a sugar, a wax, and a water-soluble polymer can complete the dissolution of the whole of the drug within a given short time in pseudo zero-order release pattern, and have demonstrated that the drug composition succeeded in a sustained-release without lowering the bioavailability in an actual pharmacokinetic test with a dog. Based upon the new findings, the present invention has been completed.

The present invention can show as follows.

(Term 1)

A sustained-release composition intended for animal use, comprising (i) a drug, (ii) a sugar, (iii) a wax, and (iv) a water-soluble polymer.

(Term 2)

The sustained-release composition of Term 1, wherein the (ii) sugar is one or more selected from isomalt, mannitol, lactose, sucrose, glucose, and sorbitol.

A preferred example of the sugar includes isomalt, mannitol, and lactose, more preferably isomalt.

(Term 3)

The sustained-release composition of Term 1 or 2, wherein the (iii) wax is one or more selected from hydrogenated castor oil, hydrogenated rapeseed oil, carnauba wax, stearic acid, and sodium stearyl fumarate.

A preferred example of the wax includes hydrogenated castor oil.

(Term 4)

The sustained-release composition of any one of Terms 1-3, wherein the (iv) water-soluble polymer is one or more selected from gum arabic, xanthane gum, hydroxypropylcellulose (HPC), hydroxypropylmethylcellulose (HPMC), and methylcellulose (MC).

A preferred example of the water-soluble polymer includes gum arabic, hydroxypropylcellulose (HPC), and methylcellulose (MC), more preferably gum arabic, hydroxypropylcellulose (HPC), even more preferably gum arabic.

(Term 5)

The sustained-release composition of any one of Terms 1-4, wherein the content of the (i) drug is 10 wt %-90 wt %, the content of the (ii) sugar is 5 wt %-90 wt %, the content of the (iii) wax is 0.5 wt %-70 wt %, and the content of the (iv) water-soluble polymer is 2 wt %-80 wt %.

(Term 6)

The sustained-release composition of any one of Terms 1-4, wherein the content of the (i) drug is 15 wt %-80 wt %, the content of the (ii) sugar is 10 wt %-80 wt %, the content of the (iii) wax is 1 wt %-60 wt %, and the content of the (iv) water-soluble polymer is 4 wt %-70 wt %.

(Term 7)

The sustained-release composition of any one of Terms 1-4, wherein the content of the (i) drug is 20 wt %-70 wt %, the content of the (ii) sugar is 15 wt %-70 wt %, the content of the (iii) wax is 1.5 wt %-50 wt %, and the content of the (iv) water-soluble polymer is 6 wt %-60 wt %.

(Term 8)

The sustained-release composition of any one of Terms 1-7, wherein the animal belongs to Carnivora.

The animal belonging to Carnivora includes, for example, a pet animal which likes eating meat on a routine basis, more specifically dogs and cats, more preferably dogs.

(Term 9)

The sustained-release composition of any one of Terms 1-8, whose formulation is a tablet.

(Term 10)

The sustained-release composition of any one of Terms 1-9, wherein the (1) drug is zonisamide.

(Term 11)

The sustained-release composition of any one of terms 1-10, which further comprises a lubricant.

(Term 12)

The sustained-release composition of any one of terms 1-11, wherein the dissolution rate in dissolution test of the composition shows a pseudo zero-order release for 1-9 hours.

The dissolution test herein is intended to the dissolution test shown in the examples below. Preferably, it shows a pseudo zero-order release for 1.5-6 hours, more preferably a pseudo zero-order release for 2-5 hours.

Effect of the Invention

Normal quick-release formulations give a burst-like release in early dissolution. On the other hand, normal sustained-release formulations give a controlled release rate depending on the size of tablet in early dissolution, but the release rate tends to delay gradually in late dissolution because the surface area of the tablet decreases and thereby the release rate in early dissolution cannot be maintained in late dissolution. In addition, the dissolution of membrane-controlled sustained-release formulations is generally controlled under favor of the concentration difference between inside and outside of the membrane, but the release rate thereof also tends to delay gradually in late dissolution because the concentration of the inside decreases.

The composition of the present invention does not produce a burst-like release in early dissolution and does not create a delay in late dissolution, that is, the present composition can realize pseudo zero-order release, which can make a drug therein dissolved at a constant rate independent of time course and make all the drug dissolved out in a given period. In addition, the rate of the pseudo zero-order release can be controlled by adjusting the composition of each ingredient, the composition amount, and the mixing ratio. For example, it is possible to prepare a drug formulation which can complete the dissolution in about 3 hours or in another period, which means that it is possible to prepare any ideal compositions suitable for each animal type.

It is guessed that the above-mentioned effect of the present invention can be achieved through the difference of solubility in the type of additives, as follows: in early dissolution, an easily-dissoluble part in the tablet disintegrates/dissolves to make the drug at the surface of the table dissolved at a constant rate; as the dissolution progressed, the drug in the tablet inside is also dissolved; in late dissolution, hardly-dissoluble additives in the tablet gradually weaken, and in the end the whole tablet completely disintegrates to dissolve out all the drug. In the present invention, it is guessed that the dissolution behavior is made to become pseudo zero-order release by suitably-specifying the composition of each ingredient, the composition amount, and the mixing ratio.

DESCRIPTION OF EMBODIMENTS

Figure 1:
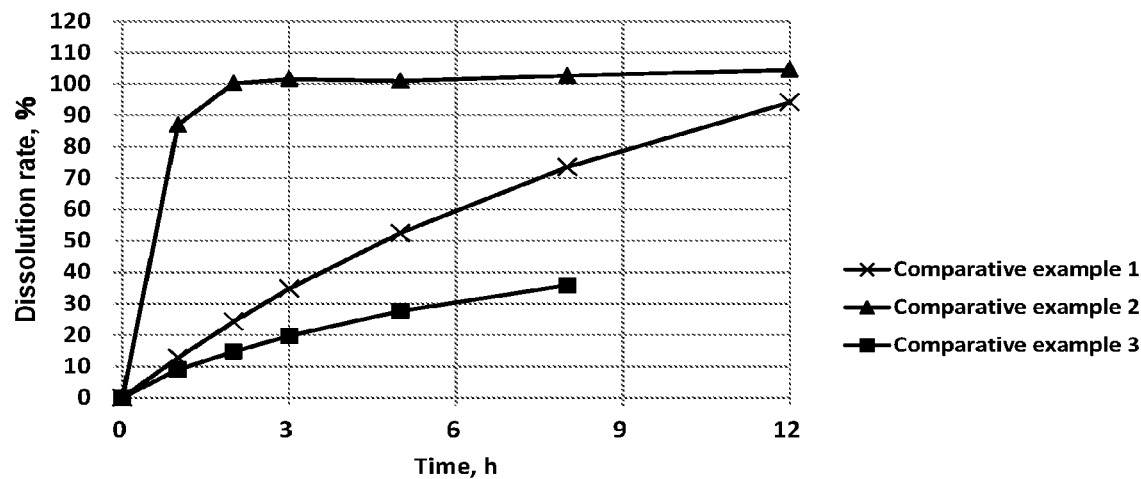
FIG. 1 shows results of Comparative examples 1-3 in the dissolution test using 2nd fluid for dissolution test (pH 6.8 buffer).

Hereinafter, the present invention is explained showing the meanings of the terms used herein and the embodiments thereof.

The drug used herein includes drugs for a chronic disease in a pet animal such as dogs, which can suppress its symptom through the daily administration. It includes, for example, antiepileptic agents such as zonisamide and imepitoin, medicaments for treating heart failure such as pimobendan and alacepril, and prokinetic agents such as mosapride; preferably it is antiepileptic agents, particularly zonisamide. In the present invention, however, it should not be construed to be limited to these drugs. Any drugs may be used herein as long as they are drugs intended for animal use for suppressing a symptom of a chronic disease through the daily administration.

The amount of a drug in the present invention may be chosen from 10 wt %-90 wt % per the whole weight of its formulation, and preferably 15 wt %-80 wt %, more preferably 20 wt %-70 wt %.

The sugar used herein should not be limited as long as it is a normal sugar used as a pharmaceutical additive, and it includes, for example, one or more selected from isomalt, mannitol, lactose, sucrose, glucose, and sorbitol; preferably isomalt, mannitol, and lactose; more preferably isomalt.

In more detail, isomalt includes Galen IQ720 (HIGUCHI INC.), Galen IQ721 (HIGUCHI INC.), Galen IQ800 (HIGUCHI INC.), Galen IQ810 (HIGUCHI INC.), and Isomalt Powder for direct tableting (MICROFOODS JAPAN).

The amount of a sugar in the present invention may be chosen from 5 wt %-90 wt % per the whole weight of its formulation, and preferably 10 wt %-80 wt %, more preferably 15 wt %-70 wt %.

The wax used herein should not be limited as long as it is a normal wax used as a pharmaceutical additive, and it includes, for example, one or more selected from hydrogenated castor oil, hydrogenated rapeseed oil, carnauba wax, stearic acid, and sodium stearyl fumarate; preferably hydrogenated castor oil.

In more detail, hydrogenated castor oil includes Libriwax 101 (FREUND CORPORATION), hydrogenated rapeseed oil includes Libriwax 103 (FREUND CORPORATION), carnauba wax includes Polidhing wax 105 (FREUND CORPORATION), stearic acid includes stearic acid provided by Mallinckrodt Pharmaceuticals, and sodium stearyl fumarate includes PRUV (Kimura Sangyo Co., Ltd).

The amount of a wax in the present invention may be chosen from 0.5 wt %-70 wt % per the whole weight of its formulation, and preferably 1 wt-60 wt %, more preferably 1.5 wt %-50 wt %.

The water-soluble polymer used herein should not be limited as long as it is a normal water-soluble polymer used as a pharmaceutical additive, and it includes, for example, one or more selected from gum arabic, xanthan gum, hydroxypropylcellulose (HPC), hydroxypropylmethylcellulose (HPMC), and methylcellulose (MC); preferably gum arabic, hydroxypropylcellulose (HPC), methylcellulose (MC); more preferably gum arabic, hydroxypropylcellulose (HPC); even more preferably gum arabic. In addition, polyvinylpyrrolidone (PVP), polyvinyl alcohol (PVA), polyethylene glycol (PEG), dextran, pullulan, pectin, and the like may be also used as the water-soluble polymer of the present invention.

In more detail, gum arabic includes Gum Arabic spray (NIPPON FUNMATSU YAKUHIN Co., LTD.) and Arabic kohl SS (SAN-EI YAKUHIN BOEKI CO., LTD); xanthane gum includes xanthane gum provided by DSP GOKYO FOOD & CHEMICAL CO., LTD.; hydroxypropylcellulose includes HPC-LFP (NIPPON SODA CO., LTD.), HPC-SSL (NIPPON SODA CO., LTD.), HPC-L(NIPPON SODA CO., LTD.), HPC-M (NIPPON SODA CO., LTD.), and HPC-H (NIPPON SODA CO., LTD.); hydroxypropylmethylcellulose includes HPMC and TC5-R (Shin-Etsu Chemical Co., Ltd.); and methylcellulose includes SM-4, SM-15, SM-25, SM-100, SM-400, SM-1500, SM-4000, 60SH-50, 60SH-4000, 60SH-10000, 65SH-50, 65SH-400, 65SH-4000, 90SH-100SR, 90SH-4000SR, 90SH-15000SR, and 90SH-100000SR.

The amount of a water-soluble polymer in the present invention may be chosen from 2 wt %-80 wt % per the whole weight of its formulation, and preferably 4 wt %-70 wt %, more preferably 6 wt %-60 wt %.

In addition, the composition of the present invention may comprise a general additive for drug product unless the zero-order release behavior is adversely affected, said additive includes, for example, lubricant, carrier, binder, flavor, buffer, thickener, colorant, stabilizer, emulsifier, dispersant, suspending agent, and preservative.

Widely-used lubricant herein includes light anhydrous silicic acid, magnesium stearate, and sodium stearyl fumarate; and in more detail, light anhydrous silicic acid includes Aerosil 200 (NIPPON AEROSIL CO., LTD); magnesium stearate includes magnesium stearate (vegetable grade) (Taihei Chemical Industrial Co., Ltd.); and sodium stearyl fumarate includes PRUV (Kimura Sangyo Co., Ltd).

The animal in "for animal use" is intended for Carnivora that have relatively short gastrointestinal tract, which include, for example, pet animals such as dogs and cats, preferably dogs. However, it should not be limited to these animals, and it may be used for other animals.

The "sustained-release composition" in the present invention is intended to be an oral solid formulation which includes, for example, a tablet, a capsule, and a granule, preferably a tablet. The tablet may be film-coated.

The "sustained-release composition" in the present invention can be prepared in a standard manner of formulation production. Preferably, the tablet includes a plain tablet. The production of a tablet includes, for example, mixing each ingredient in an appropriate mixer, and tableting the mixture with a tableting machine using a suitable punch. As another production, a tablet may be also prepared as follows; wet-granulating a portion or all of ingredients in a granulator, adding the other ingredients to the granulated mixture and mixing it if the other ingredients exist, and tableting it with a tableting machine. However, it should not be limited to these productions.

The "zero-order release" in the present invention means that the dissolution rate in a dissolution test increases linearly with time, and for example, if 100% dissolution is established in 100 minutes, 25%, 50%, and 75% dissolutions are established in 25, 50, and 75 minutes, respectively. Thus, the zero-order release means that a formulation product does not give a burst-like release in early dissolution, and complete the dissolution sharply in late dissolution, and the pseudo zero-order release shows a similar dissolution behavior to it.

EXAMPLES

In order to show the effect of the present invention, Comparative examples, Examples, and Test example are shown as just examples in the following, but the present invention should not be limited thereto in any cases. A skilled person may perform the present invention optionally by modifying the conditions defined in the following working examples, and such modification should be encompassed in the claims of the present application.

Comparative Examples 1-3

(Preparation)

Each ingredient listed in the table below is weighed. The weighed hydrogenated castor oil and magnesium stearate are screened with 30-mesh-screen, and the screened ingredients are mixed with the other ingredient(s) in a polyethylene bag.

The prepared powder is tableted with a hydraulic tableting machine wherein the diameter of the punch is 6 mm and the tableting pressure is 5 kN.

| Ingredient | Comparative example 1 mg | Comparative example 2 mg | Comparative example 3 mg |
|---|---|---|---|
| zonisamide | 50 | 50 | 50 |
| isomalt (Galen IQ720) | — | 49.5 | — |
| hydrogenated castor oil | — | — | 10 |
| magnesium stearate | 0.25 | 0.5 | 0.3 |
| total | 50.25 | 100 | 60.3 |
| Total amount of actual production | 20.1 g | 20 g | 12.6g |

(Dissolution Test)

The dissolution test with each test tablet was carried out according to Dissolution Test <6.10> in the Japanese Pharmacopoeia 16th Edition (Paddle Method 100 rpm, Dissolution Medium: 2nd fluid for dissolution test (pH 6.8 buffer)). The assay of the active ingredient (zonisamide) in the test sample was carried out according to Liquid Chromatography (HPLC) <2.01> in the Japanese Pharmacopoeia 16th Edition, and the detailed condition of the assay was based on the assay of "zonisamide" in the Japanese Pharmaceutical Codex (2002). The dissolution tests of Examples 1-20 shown below were carried out in the same manner. As for Example 20, additional dissolution tests were also carried out with 1st fluid for dissolution test (pH 1.2 buffer), pH 4.0 buffer, and water as dissolution medium.

(Result)

The result of the dissolution tests with the test tablets is shown in FIG. 1.

Comparative example 1 which was a tablet substantially-consisting of zonisamide exhibited a considerable sustained-release property, but the tablet hardness thereof was real 0 N (newton), which means that it had no quality for practical tablets. Comparative example 2 which was a formulation-type comprising zonisamide and a sugar exhibited an extremely rapid dissolution rate. However, the tablet hardness thereof became practicable by adding a sugar to zonisamide. Comparative example 3 which was a formulation-type comprising zonisamide and a wax exhibited an extremely late dissolution rate.

Examples 1-3

(Preparation)

Each ingredient listed in the table below is weighed. The weighed hydrogenated castor oil and magnesium stearate are screened with 30-mesh-screen, and the screened ingredients are mixed with the other ingredients in a polyethylene bag. The prepared powder is tableted with a hydraulic tableting machine wherein the diameter of the punch is 7 mm and the tableting pressure is 6 kN.

| Ingredient | Example 1 mg | Example 2 mg | Example 3 mg |
|---|---|---|---|
| zonisamide | 50 | 50 | 50 |
| isomalt (Galen IQ720) | 70.4 | 68.3 | 66.9 |
| hydrogenated castor oil | 4.9 | 7 | 8.4 |
| gum arabic | 14 | 14 | 14 |
| magnesium stearate | 0.7 | 0.7 | 0.7 |
| total | 140 | 140 | 140 |
| Total amount of actual production | 28 g | 28 g | 28 g |

(Result)

Figure 2:
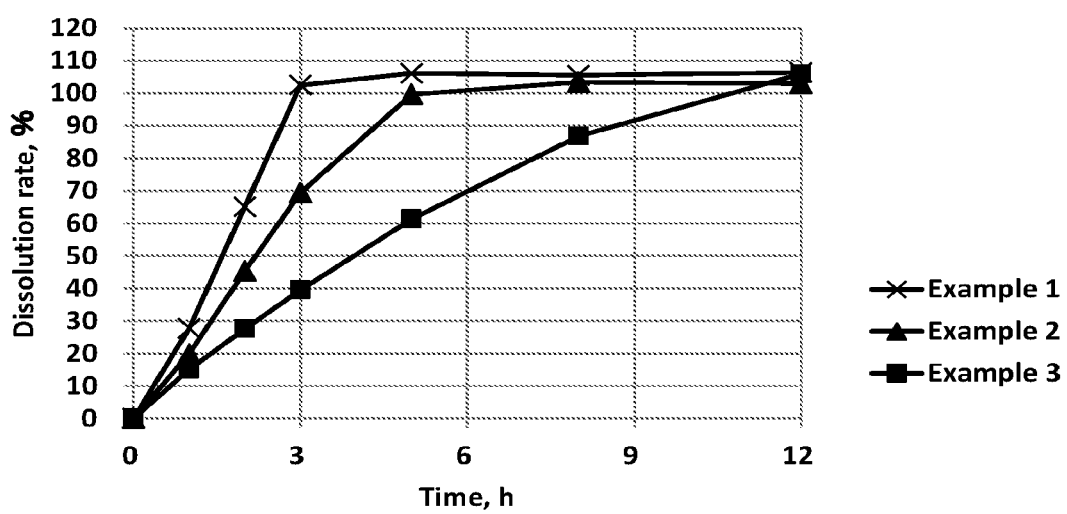
FIG. 2 shows results of Examples 1-3 in the dissolution test using 2nd fluid for dissolution test (pH 6.8 buffer).

The result of the dissolution tests with the test tablets is shown in FIG. 2.

In this test, the quantitative influence of hydrogenated castor oil which was added as a wax was studied in formulation-types comprising isomalt+hydrogenated castor oil+gum arabic as additives. The formulation prepared in Example 1 substantially exhibited a targeted zero-order release property in three hours. The property of the present formulation is to complete almost 100% dissolution of a drug at the end of the zero-order release. It is for preventing the shortfall of gastrointestinal absorption in dogs because their gastrointestinal tract has a restricted length. The concept of the present invention was accomplished in Example 1. In addition, it has been found that the increase of the wax ratio makes it possible to control the termination time of dissolution freely, like Example 2 and Example 3.

Examples 4 and 5

(Preparation)

Each ingredient listed in the table below is weighed. The weighed hydrogenated castor oil and magnesium stearate are screened with 30-mesh-screen, and the screened ingredients are mixed with the other ingredients in a polyethylene bag. The prepared powder is tableted with a hydraulic tableting machine wherein the diameter of the punch is 7 mm and the tableting pressure is 6 kN.

| Ingredient | Example 4 mg | Example 5 mg |
|---|---|---|
| zonisamide | 50 | 50 |
| isomalt (Galen IQ720) | 61.3 | 54.3 |
| hydrogenated castor oil | 7 | 7 |
| gum arabic | 21 | 28 |
| magnesium stearate | 0.7 | 0.7 |
| total | 140 | 140 |
| Total amount of actual production | 28 g | 28 g |

(Result)

Figure 3:
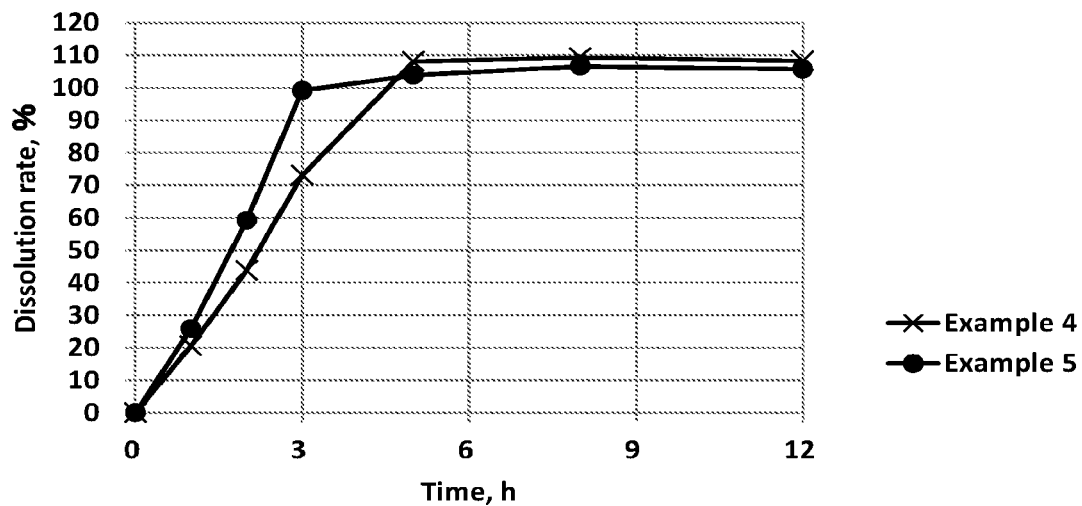
FIG. 3 shows results of Examples 4 and 5 in the dissolution test using 2nd fluid for dissolution test (pH 6.8 buffer).

The result of the dissolution tests with the test tablets is shown in FIG. 3.

In this test, the quantitative influence of gum arabic which was added as a water-soluble polymer was studied in formulation-types comprising isomalt+hydrogenated castor oil+gum arabic as additives. There was not so big difference in the dissolution results of Examples 2, 4, and 5 which had different amounts of gum arabic. It is thought that gum arabic as a water-soluble polymer serves as a dissolution regulator which can make the dissolution (of a tablet comprising a sugar and a wax) a natural zero-order release by easing an extreme variation.

Examples 6-8

(Preparation)

Each ingredient listed in the table below is weighed. The weighed carnauba wax, stearic acid, sodium stearyl fumarate, and magnesium stearate are screened with 30-mesh-screen, and the screened ingredients are mixed with the other ingredients in a polyethylene bag. The prepared powder is tableted with a hydraulic tableting machine wherein the diameter of the punch is 7 mm and the tableting pressure is 6 kN.

| Ingredient | Example 6 mg | Example 7 mg | Example 8 mg |
|---|---|---|---|
| zonisamide | 50 | 50 | 50 |
| isomalt (Galen IQ720) | 69.7 | 65.3 | 65.3 |
| carnauba wax | 5.6 | — | — |
| stearic acid | — | 10 | — |
| sodium stearyl fumarate | — | — | 10 |
| gum arabic | 14 | 14 | 14 |
| magnesium stearate | 0.7 | 0.7 | 0.7 |
| total | 140 | 140 | 140 |
| Total amount of actual production | 28 g | 28 g | 28 g |

(Result)

Figure 4:
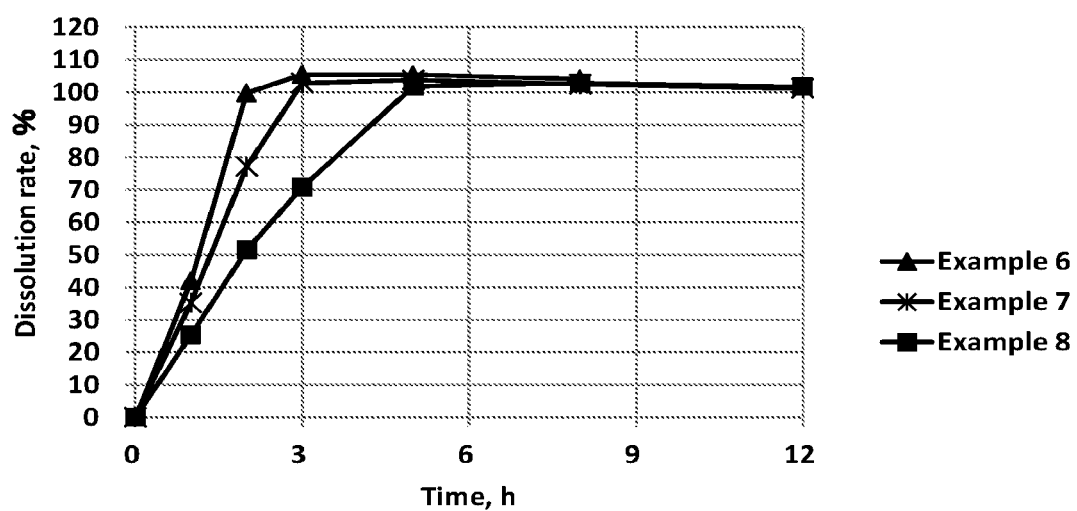
FIG. 4 shows results of Examples 6-8 in the dissolution test using 2nd fluid for dissolution test (pH 6.8 buffer).

The result of the dissolution tests with the test tablets is shown in FIG. 4.

In this test, the influence of type of a wax on the dissolution profile (with carnauba wax, stearic acid, and sodium stearyl fumarate) was studied in formulation-types comprising isomalt+a wax+gum arabic as additives. Each end point in the dissolution tests was well controlled, which varied depending on the property of each wax.

Examples 9 and 10

(Preparation)

Each ingredient listed in the table below is weighed. The weighed hydroxypropylcellulose (HPC LFP and HPC SSL), hydrogenated castor oil, and magnesium stearate are screened with 30-mesh-screen, and the screened ingredients are mixed with the other ingredients in a polyethylene bag. The prepared powder is tableted with a hydraulic tableting machine wherein the diameter of the punch is 7 mm and the tableting pressure is 6 kN.

| Ingredient | Example 9 mg | Example 10 mg |
|---|---|---|
| zonisamide | 50 | 50 |
| isomalt (Galen IQ720) | 69.7 | 61.3 |
| hydrogenated castor oil | 5.6 | 5.6 |
| hydroxypropylcellulose (HPC LFP) | 14 | — |
| hydroxypropylcellulose (HPC SSL) | — | 14 |
| magnesium stearate | 0.7 | 0.7 |
| total | 140 | 140 |
| Total amount of actual production | 28 g | 28 g |

(Result)

Figure 5:
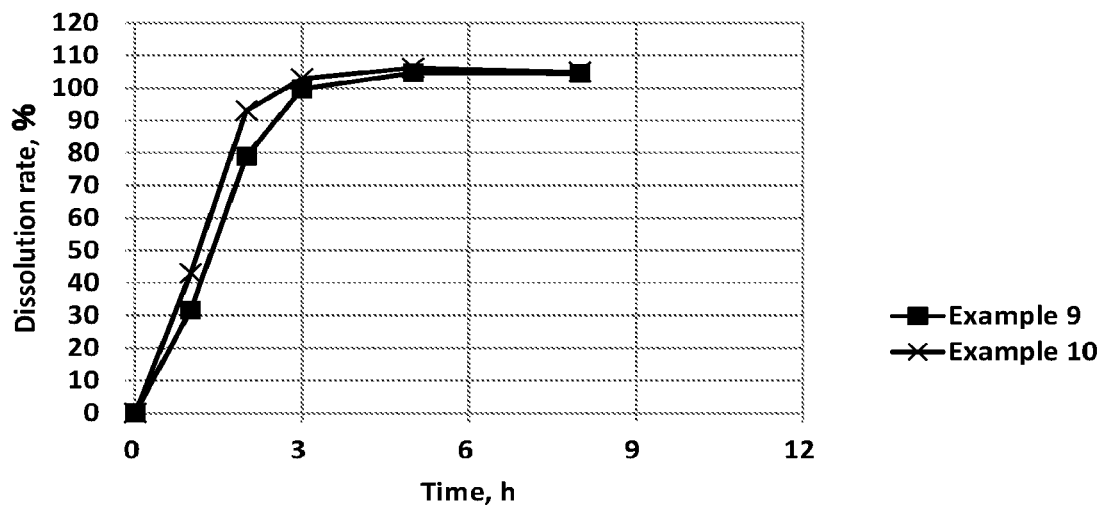
FIG. 5 shows results of Examples 9 and 10 in the dissolution test using 2nd fluid for dissolution test (pH 6.8 buffer).

The result of the dissolution tests with the test tablets is shown in FIG. 5.

In this test, the influence of type of hydroxypropylcellulose (HPC) which was added as a water-soluble polymer (with HPC-LFP and HPC-SSL) was studied in formulation-types comprising isomalt+hydrogenated castor oil+water-soluble polymer as additives. The both examples exhibited dissolution behavior close to zero-order dissolution rate at the termination point (about 3 hours) was almost 100%.

Examples 11-13

(Preparation)

Each ingredient listed in the table below is weighed. The weighed hydrogenated castor oil and magnesium stearate are screened with 30-mesh-screen, and the screened ingredients are mixed with the other ingredients in a polyethylene bag. As for Examples 11-12, the prepared powder is tableted with a rotary tableting machine wherein the diameter of the punch is 6 mm and the tableting pressure is 5 kN. As for Example 13, the prepared powder is tableted with a hydraulic tableting machine wherein the diameter of the punch is 6 mm and the tableting pressure is 5 kN.

| Ingredient | Example 11 mg | Example 12 mg | Example 13 mg |
|---|---|---|---|
| zonisamide | 50 | 50 | 50 |
| lactose (SUPER TAB 11SD) | 38.5 | 38 | 34.5 |
| hydrogenated castor oil | 1 | 1.5 | 5 |
| gum arabic | 10 | 10 | 10 |
| magnesium stearate | 0.5 | 0.5 | 0.5 |
| total | 100 | 100 | 100 |
| Total amount of actual production | 400 g | 400 g | 40 g |

(Result)

Figure 6:
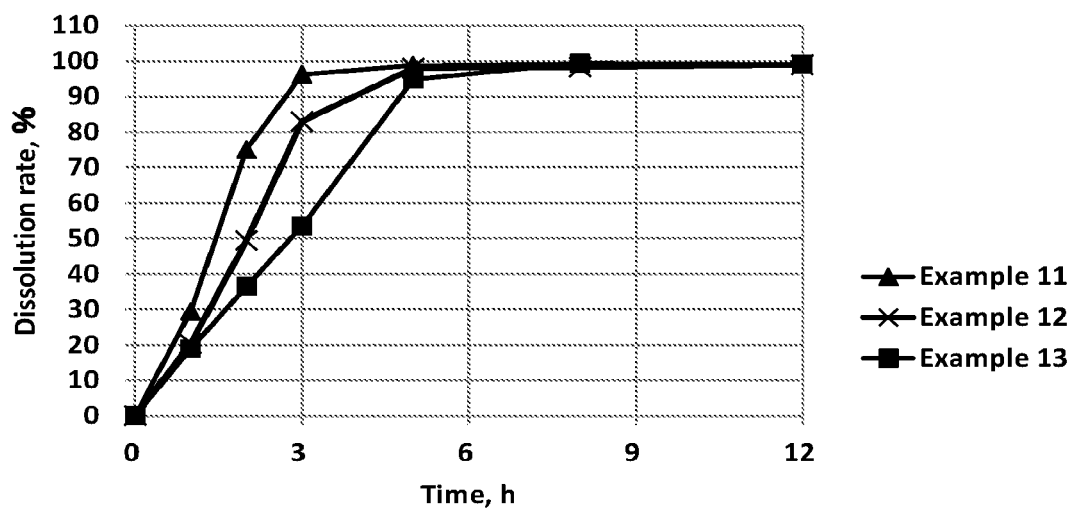
FIG. 6 shows results of Examples 11-13 in the dissolution test using 2nd fluid for dissolution test (pH 6.8 buffer).

The result of the dissolution tests with the test tablets is shown in FIG. 6.

As for formulation-types comprising a sugar hydrogenated castor oil+gum arabic as additives wherein the sugar is lactose (SUPER TAB 11SD), the termination points of the zero-order release were controlled at around 3 hours in Examples 11-12, and at a little later in Example 13. The termination point of the zero-order release was able to be controlled by adjusting the amount of hydrogenated castor oil used herein.

Examples 14-16

(Preparation)

Each ingredient listed in the table below is weighed. The weighed hydrogenated castor oil and magnesium stearate are screened with 30-mesh-screen, and the screened ingredients are mixed with the other ingredients in a polyethylene bag. As for Example 14, the prepared powder is tableted with a hydraulic tableting machine wherein the diameter of the punch is 6 mm and the tableting pressure is 5 kN. As for Examples 15 and 16, the prepared powder is tableted with a hydraulic tableting machine wherein the diameter of the punch is 7 mm and the tableting pressure is 6 kN.

| Ingredient | Example 14 mg | Example 15 mg | Example 16 mg |
|---|---|---|---|
| zonisamide | 50 | 50 | 50 |
| isomalt (Galen IQ800) | 36 | — | — |
| isomalt (Isomalt Powder for direct tableting) | — | 69.7 | — |
| D-mannitol (PEARLITOL 100SD) | — | — | 66.3 |

-continued

| Ingredient | Example 14 mg | Example 15 mg | Example 16 mg |
|---|---|---|---|
| hydrogenated castor oil | 3.5 | 5.6 | 9 |
| gum arabic powder | 10 | 14 | 14 |
| magnesium stearate | 0.5 | 0.7 | 0.7 |
| total | 100 | 140 | 140 |
| Total amount of actual production | 20 g | 28 g | 28 g |

(Result)

Figure 7:
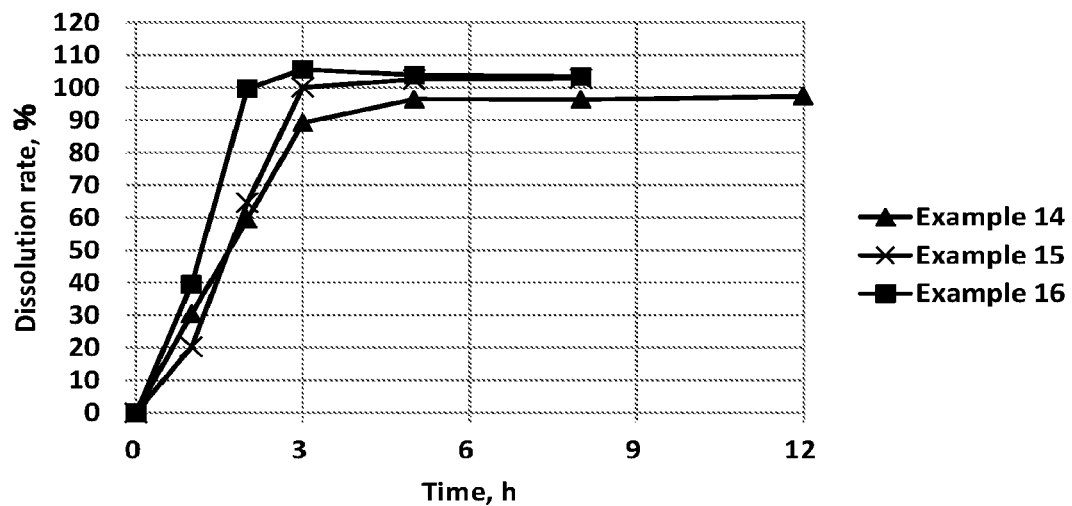
FIG. 7 shows results of Examples 14-16 in the dissolution test using 2nd fluid for dissolution test (pH 6.8 buffer).

The result of the dissolution tests with the test tablets is shown in FIG. 7.

In this test, the influence of type of a sugar was studied in formulation-types comprising a sugar hydrogenated castor oil+gum arabic as additives, by using two kinds of isomalt as the sugar which are provided by different vendors (Galen IQ800, and Isomalt Powder for direct tableting) and D-mannitol (PEARLITOL 100SD). In Examples 14 and 15 which both comprise isomalt, the dissolution rates were controlled to complete the dissolution in about three hours. Example 16 using D-mannitol exhibited a little rapid dissolution, but said dissolution was controlled.

Examples 17-19

(Preparation)

Each ingredient listed in the table below is weighed. The weighed hydrogenated castor oil and magnesium stearate are screened with 30-mesh-screen, and the screened ingredients are mixed with the other ingredients in a V blender. The prepared powder is tableted with a hydraulic tableting machine wherein the diameter of the punch is 7 mm, mm, or 12 mm, for 50 mg, 100 mg, or 200 mg tablet, respectively, and the tableting pressure is 6 kN, 9 kN, or 14 kN, for 50 mg, 100 mg, or 200 mg tablet, respectively.

| Ingredient | Example 17 mg | Example 18 mg | Example 19 mg |
|---|---|---|---|
| zonisamide | 50 | 100 | 200 |
| isomalt (Galen IQ720) | 69 | 138 | 276 |
| hydrogenated castor oil | 5.6 | 11.2 | 22.4 |
| gum arabic | 14 | 28 | 56 |
| light anhydrous silicic acid | 0.7 | 1.4 | 2.8 |
| magnesium stearate | 0.7 | 1.4 | 2.8 |
| total | 140 | 280 | 560 |
| Total amount of actual production | 280 g | 280 g | 280 g |

(Result)

Figure 8:
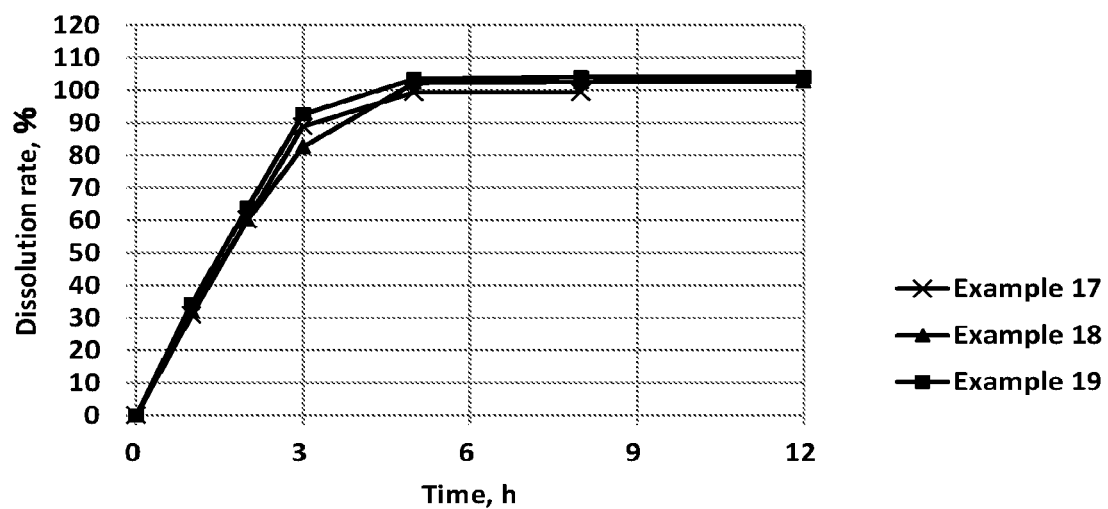
FIG. 8 shows results of Examples 17-19 in the dissolution test using 2nd fluid for dissolution test (pH 6.8 buffer).

The result of the dissolution tests with the test tablets is shown in FIG. 8.

Formulations comprising isomalt+hydrogenated castor oil+gum arabic as additives in which the tablet size varied between 50 mg tablet-200 mg tablet were prepared. Each terminate time in the dissolution tests was controlled to about three hours.

Example 20

(Preparation)

Each ingredient listed in the table below is weighed. The weighed hydrogenated castor oil and magnesium stearate are screened with 30-mesh-screen, and the screened ingredients are mixed with the other ingredients in a polyethylene bag. As for Example 20, the prepared powder is tableted with a rotary tableting machine wherein the diameter of the punch is 7 mm and the tableting pressure is 6 kN.

| Ingredient | Example 20 mg |
|---|---|
| zonisamide | 50 |
| isomalt (Galen IQ720) | 69.7 |
| hydrogenated castor oil | 5.6 |
| gum arabic | 14 |
| magnesium stearate | 0.7 |
| total | 140 |
| Total amount of actual production | 280 g |

(Result)

Figure 9:
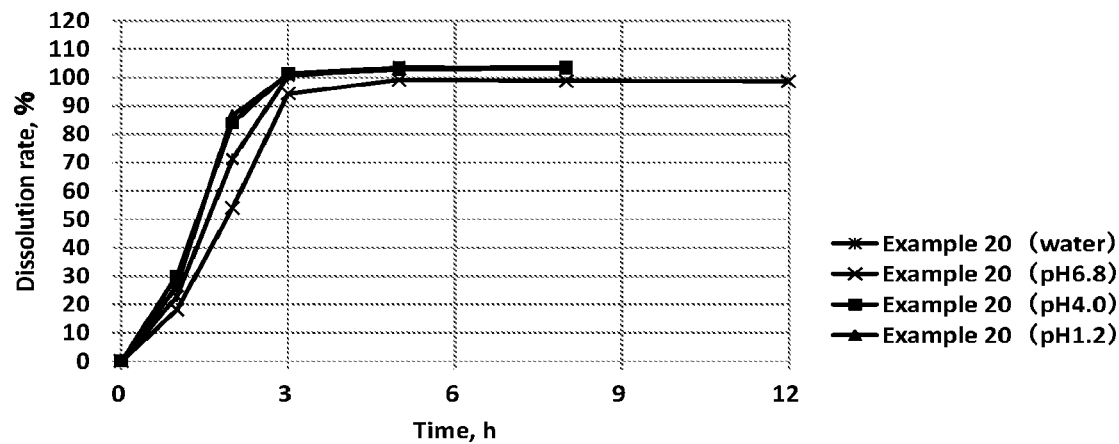
FIG. 9 shows results of Example 20 in the dissolution test using pH 1.2, pH 4.0, pH 6.8 buffers and water as the test media.

The result of the dissolution tests with the test tablet is shown in FIG. 9.

Using the tablet of Example 20, the dissolution tests were carried out with pH 1.2 buffer, pH 4.0 buffer, pH 6.8 buffer, and water as the dissolution medium.

This result has clarified that the present sustained-release tablet of zonisamide is little influenced by dissolution test media.

Test 1

(Pharmacokinetic Study Through Single Administration to Dog)

The rapid-release commercial tablet of zonisamide or the sustained-release tablet prepared herein (Example 20) was orally administered to a dog, and each pharmacokinetics (hereinafter, mentioned as "PK") was tested. Specifically, first of all, a rapid-release tablet of 100 mg zonisamide (which is equivalent of the commercial product tablet) used as a reference drug was prepared, and the rapid-release tablet was administered to 4 beagle dogs which were fasted for at least 16 hours before the administration (100 mg×1 tablet per one dog), with 10 mL of water. 30 minutes, 1, 2, 3, 4, 6, 9, 12, 24, 36, 48, and 72 hours after the administration, every about 2 mL of blood was collected as whole blood. Four hours after the administration, the dogs were fed. After that, the dogs were fed once a day at a fixed time. The plasma was divided from each collected blood, and the drug concentration of each plasma was measured by liquid chromatography (HPLC).

After the test with the reference drug, the same beagle dogs were given 2-week washout period, and then the sustained-release tablet of 50 mg zonisamide prepared in Example 20 was administered to the beagle dogs which were fasted for at least 16 hours before the administration (50 mg×4 tablets per one dog), with 10 mL of water. 1, 2, 3, 4, 6, 8, 10, 12, 24, 36, 48, and 72 after the administration, every about 2 mL of blood was collected as whole blood. After the administration, the dogs were fed as is the case with the rapid-release tablet test. The drug concentration was also measured by liquid chromatography (HPLC) as is the case with the rapid-release tablet test.

(Result)

Figure 10:
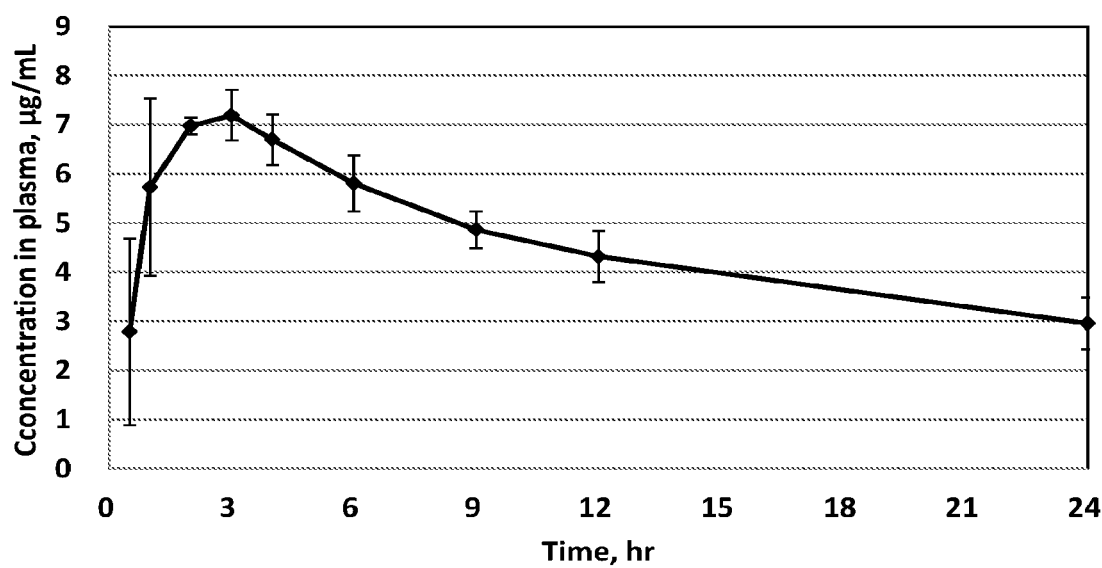
FIG. 10 shows the concentration-variations of zonisamide in plasma in Test 1 wherein quick-release zonisamide tablet 100 mg×1 tablet (100 mg single) was administered.
Figure 11:
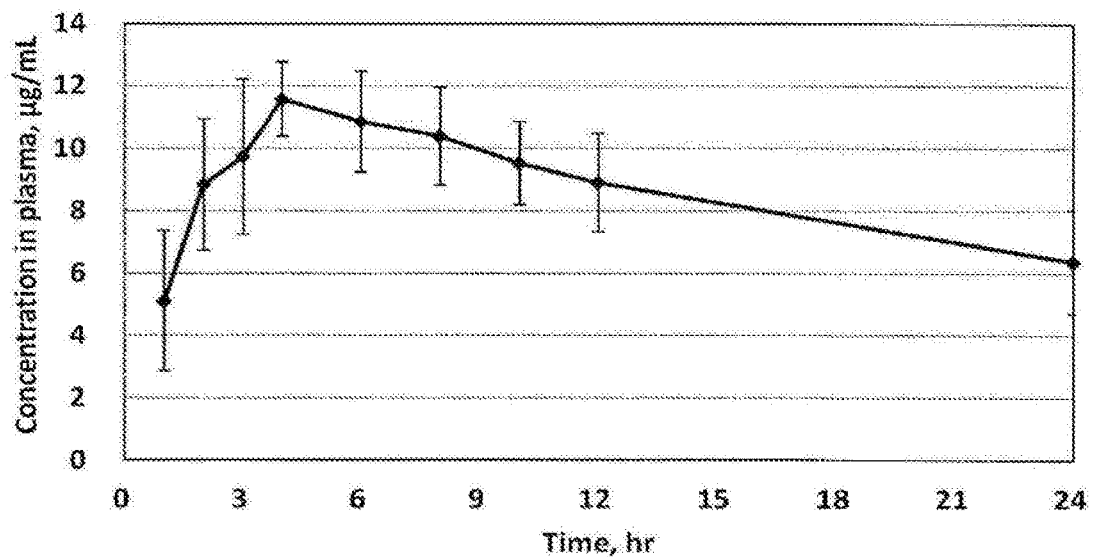
FIG. 11 shows the concentration-variations of zonisamide in plasma in Test 1 wherein sustained-release zonisamide tablet 50 mg×4 tablets (200 mg single) was administered.

As for the results of the rapid-release tablet and the sustained-release tablet, the concentration-variations of zonisamide in plasma for 24 hours are shown in FIGS. 10 and 11 (in which the data were meanscores from each four dogs). As for each PK parameter in the single administration, maximum plasma concentration (Cmax), time-to-maximum plasma concentration (Tmax), area under the plasma concentration-time curve (AUC∞), elimination rate constant of plasma concentration (Kel), half-life (T1/2), and mean retention time (MRT) were estimated from the concentration-variations. And, the relative availability was estimated from the AUC ratio of the sustained-release tablet and the rapid-release tablet. These parameters are shown in the table below.

| Drug formulation | sustained-release tablet 200 mg ×1 | rapid-release tablet 100 mg ×1 |
|---|---|---|
| Cmax (µg/g) | 11.8 | 7.4 |
| Tmax (h) | 4.5 | 2.3 |
| AUC∞ (µg · h/mL) | 462.2 | 220.8 (1.05*) |
| Kel (h − 1) | 0.0400 | 0.0457 |
| T1/2 (h) | 17.6 | 15.5 |
| MRT (h) | 17.0 | 15.5 |

*relative availability = sustained/(rapid × 2)

According to the result of the single administration in the dog PK test, it has been found that the Tmax and other parameters of the sustained-release tablet are delayed, compared with the rapid-release tablet. The relative ratio of AUC is 1.05, which means that the relative bioavailability of the drug in the sustained-release tablet does not decrease.

(Presumption of Concentration Parameter in Plasma Through Simulation of Repeated Administration)

Figure 12:
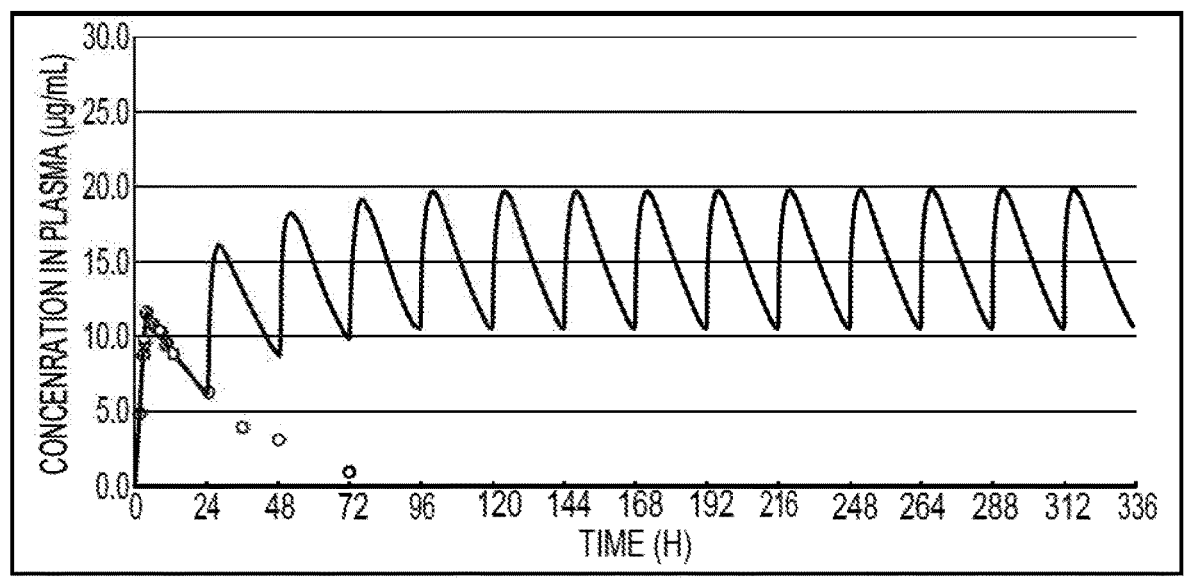
FIG. 12 shows a simulation of the concentration-variations of zonisamide in plasma in Test 1 wherein sustained-release 200 mg tablet is repeatedly administered once a day.
Figure 13:
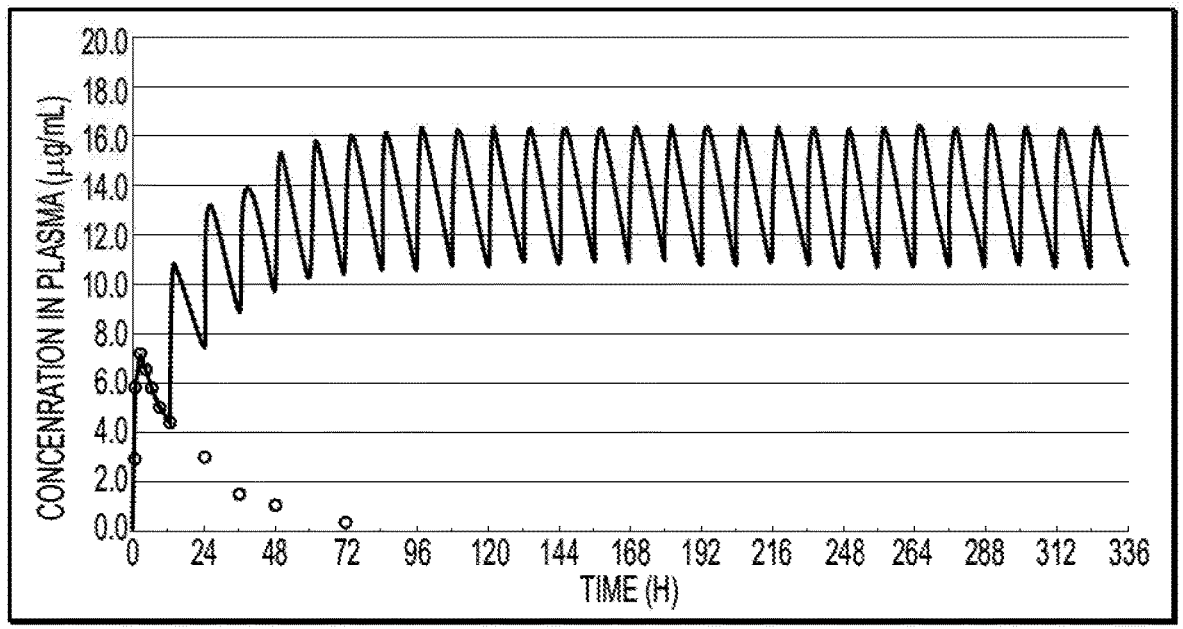
FIG. 13 shows a simulation of the concentration-variations of zonisamide in plasma in Test 1 wherein quick-release 100 mg tablet is repeatedly administered twice a day.
Figure 14:
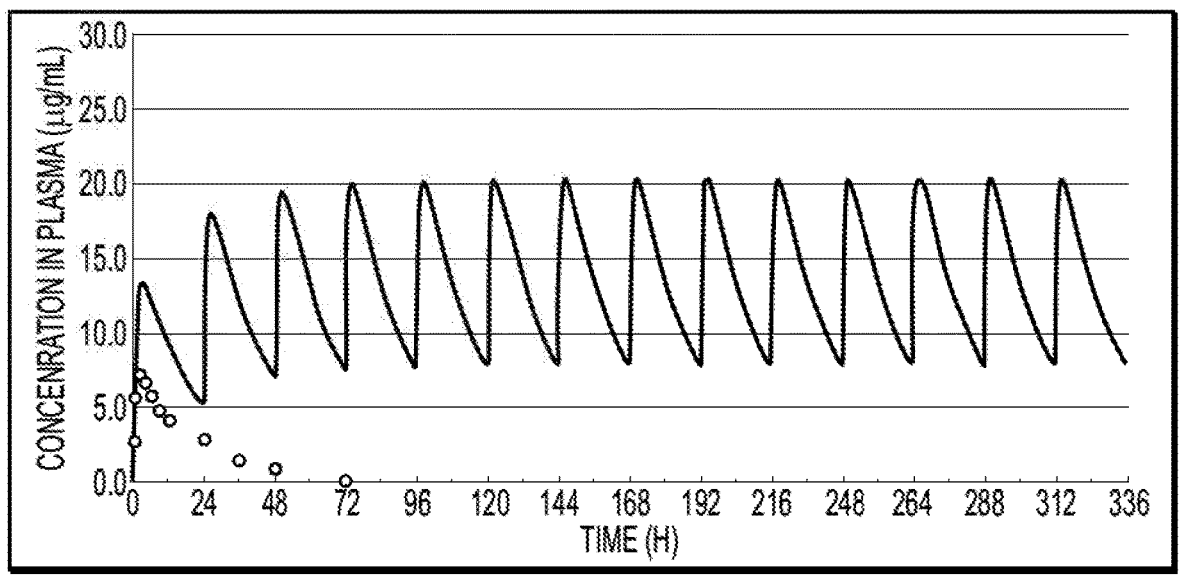
FIG. 14 shows a simulation of the concentration-variations of zonisamide in plasma in Test 1 wherein quick-release 200 mg tablet is repeatedly administered once a day.

Further to the above experiment, in order to estimate the PK in a steady state wherein the drug is repeatedly administered, a simulation of the concentration-variations of zonisamide in plasma wherein sustained-release tablet of 200 mg zonisamide is administered once a day is shown in FIG. 12, a simulation of the concentration-variations of zonisamide in plasma wherein rapid-release tablet of 100 mg zonisamide is administered twice a day as a reference drug is shown in FIG. 13, and a simulation of the concentration-variations of zonisamide in plasma wherein rapid-release tablet of 200 mg zonisamide is administered once a day as another reference drug is shown in FIG. 14.

And, from the fitting of the plasma level in the single administration, the elimination rate constant ke (h−1) and the absorption rate constant ka (h−1) were estimated, the plasma level in a steady state wherein the drug is repeatedly administered was estimated, and the maximum plasma level (CSS, max), minimum plasma level (CSS, min), and AUCSS, 0-24 h, in a steady state were estimated. In addition, the diurnal variation (DVSS, 24 h) of the plasma level in a steady state was estimated from CSS, max/CSS, min, in which the criterion of sustained release property is 2.0 or lower. And, from the AUC ratio between the sustained-release tablet and the rapid-release tablet in a steady state, the relative availability in a steady state wherein the drug is repeatedly administered was estimated. The results are shown in the table below.

| Drug formulation | sustained-release tablet once a day 200 mg × 1 | rapid-release tablet twice a day 100 mg × 2 | rapid-release tablet once a day 200 mg × 1 |
|---|---|---|---|
| $AUC_{SS, 0\text{-}24\,h}$ (µg · h/mL) | 369.8 (1.15*) | 322.8 (1.00*) | 332.0 |
| $C_{SS, ave}$ (µg/mL) | 15.41 | 13.45 | 13.83 |
| $C_{SS, max}$ (µg/mL) | 19.82 | 16.44 | 20.43 |
| $C_{SS, min}$ (µg/mL) | 10.45 | 10.73 | 7.79 |
| $DV_{SS, 24\,h}$ (−) ($C_{SS,max}/C_{SS,min}$) | 1.90 | 1.53 | 2.62 |

*relative availability (steady state) = sustained (once a day)/rapid (twice a day)

The ratio between $AUC_{SS,0\text{-}24h}$ (in a steady state, for 24 hours) wherein the sustained-release tablet of 200 mg zonisamide is administered once a day and $AUC_{SS,0\text{-}24h}$ wherein the rapid-release tablet of 100 mg zonisamide is administered twice a day was 1.15. This result indicates that the bioavailability of the sustained-release tablet does not decrease, compared with the rapid-release tablet.

The ratio of the diurnal variation in plasma level in a steady state of the simulation, $DV_{SS,24h}$ ($C_{SS, max}/C_{SS, min}$), is 1.53 for the rapid-release tablet of 100 mg zonisamide administered twice a day, 2.62 for the rapid-release tablet of 200 mg zonisamide administered once a day, and 1.90 for the sustained-release tablet of 200 mg zonisamide once a day. In the present invention, the criterion of diurnal variation of the present formulation is 2.0 or lower, as mentioned above. Thus, the present invention has accomplished the purpose of sustained release because the ratio is lower than the criterion.

As seen above, the simulation of repeated administration showed that the purpose of sustained release has been accomplished in the present invention, without decreasing the bioavailability. Therefore it has been found that the present formulation can make once-a-day administration possible.

The invention claimed is:

1. A method of treating epilepsy in a dog or cat, comprising administering a zero-order release composition to the dog or cat,
    wherein the zero-order release composition comprises (i) zonisamide, (ii) a sugar, (iii) a wax, and (iv) a water-soluble polymer, wherein
    (i) the content of zonisamide is 20 wt %-70 wt %,
    (ii) the sugar is at least one selected from the group consisting of isomalt, mannitol, lactose, sucrose, glucose, and sorbitol, and the content of the sugar is 15 wt %-70 wt %,
    (iii) the wax is at least one selected from the group consisting of hydrogenated castor oil, hydrogenated rapeseed oil, carnauba wax, stearic acid, and sodium stearyl fumarate, and the content of the wax is 1.5 wt %-50 wt %,
    (iv) the water-soluble polymer is at least one selected from the group consisting of gum arabic, xanthane gum, hydroxypropylcellulose (HPC), hydroxypropylmethylcellulose (HPMC), and methylcellulose (MC), and the content of the water-soluble polymer is 6 wt %-60 wt %, and
    wherein the method obtains a zero-order release dissolution rate and obtains complete dissolution at about 3 hours.
2. The method according to claim 1, wherein
    (ii) the sugar is at least one selected from the group consisting of isomalt, mannitol, and lactose,
    (iii) the wax is at least one selected from the group consisting of hydrogenated castor oil, carnauba wax, stearic acid, and sodium stearyl fumarate, (iv) the water-soluble polymer is at least one selected from the group consisting of gum arabic and hydroxypropylcellulose (HPC).

3. The method according to claim 1, wherein the zero-order release composition is in the form of a tablet.

4. The method according to claim 1, wherein (ii) the sugar is isomalt.

5. The method according to claim 1, wherein (iv) the water-soluble polymer is at least one selected from the group consisting of gum arabic and hydroxypropylcellulose (HPC).

* * * * *